United States Patent [19]

Broughton et al.

[11] 4,243,683
[45] Jan. 6, 1981

[54] TERTIARY ALCOHOLS

[75] Inventors: Barbara J. Broughton, Croydon; Michael P. L. Caton, Upminster; David J. Hambling, Hornchurch, all of England

[73] Assignee: May & Baker Limited, Essex, England

[21] Appl. No.: 948,156

[22] Filed: Oct. 3, 1978

[30] Foreign Application Priority Data

Oct. 5, 1977 [GB] United Kingdom ............... 41482/77

[51] Int. Cl.³ ..................... C07C 43/23; C07C 49/835
[52] U.S. Cl. .................................... 424/331; 568/648; 568/649; 568/811; 424/337; 424/340; 424/343; 568/43; 568/308; 568/313; 568/336
[58] Field of Search ............... 260/590 R, 590 D, 592; 424/331

[56] References Cited

U.S. PATENT DOCUMENTS

| | | | |
|---|---|---|---|
| 3,706,733 | 12/1972 | Henrick et al. | 260/590 R |
| 3,755,411 | 8/1973 | Henrick et al. | 260/590 R |
| 3,828,031 | 8/1974 | Karrer | 424/331 |
| 3,904,773 | 9/1975 | Schwarz et al. | 424/331 |
| 3,978,097 | 8/1976 | Schaub et al. | 260/592 |
| 4,005,150 | 1/1977 | Sorm et al. | 260/609 F |
| 4,137,273 | 1/1979 | Siddall | 260/609 F |

*Primary Examiner*—James H. Reamer
*Attorney, Agent, or Firm*—Stevens, Davis, Miller & Mosher

[57] ABSTRACT

Tertiary alcohols of the formula:

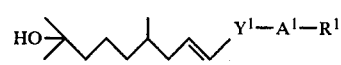

wherein $Y^1$ represents a carbonyl or hydroxymethylene group, and either (i) $A^1$ represents a direct bond and $R^1$ represents a phenyl group which may optionally carry one or more substituents selected from halogen atoms, straight- or branched-chain alkyl or alkoxy groups, each containing from 1 to 4 carbon atoms, and the trifluoromethyl group, or (ii) $A^1$ represents a straight- or branched-chain alkylene group containing from 1 to 10 carbon atoms and $R^1$ represents a hydrogen atom, or a phenyl, phenoxy or phenylthio group each of which may optionally carry one or more substituents selected from halogen atoms, straight- or branched-chain alkyl or alkoxy groups, each containing from 1 to 4 carbon atoms, and the trifluoromethyl group, are new compounds of use in the field of mammalian reproduction and also of use in the control of insects and acarines.

15 Claims, No Drawings

TERTIARY ALCOHOLS

DESCRIPTION

This invention relates to new tertiary alcohols, to processes for their preparation, to compositions containing them, to their use as pharmaceuticals, and to their use in the control of insects and acarines.

The new tertiary alcohols of the present invention are those compounds of the formula:

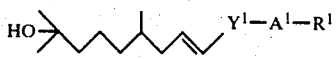

wherein $Y^1$ represents a carbonyl or hydroxymethylene group, and either (i) $A^1$ represents a direct bond and $R^1$ represents a phenyl group which may optionally carry one or more substituents selected from halogen (e.g. bromine, chlorine or iodine) atoms, straight- or branched-chain alkyl or alkoxy groups, each containing from 1 to 4 carbon atoms, and the trifluoromethyl group, or (ii) $A^1$ represents a straight- or branched-chain alkylene group containing from 1 to 10 carbon atoms and $R^1$ represents a hydrogen atom, or a phenyl, phenoxy or phenylthio group each of which may optionally carry one or more substituents selected from halogen (e.g. bromine, chlorine or iodine) atoms, straight- or branched-chain alkyl or alkoxy groups, each containing from 1 to 4 carbon atoms, and the trifluoromethyl group.

In formula I the depicted double bond is in the trans- configuration.

As will be appreciated by those skilled in the art, the structure shown in formula I has at least one center of chirality, that center of chirality being at the carbon atom connecting together the groups $HO-C(CH_3)_2-(CH_2)_3-$ and $-CH_2CH=CH-Y^1A^1R^1$. A further center of chirality occurs when $Y^1$ represents a hydroxymethylene group, and still further centers of chirality may occur in the groups $A^1$ and $R^1$. The presence of centers of chirality, as is well known, leads to the existence of isomerism. The present invention includes all such isomers and mixtures thereof.

Classes of preferred compounds of formula I are (a) those wherein $Y^1$ represents a carbonyl group;
(b) those wherein $A^1$ represents a straight-chain alkylene group containing from 1 to 3 carbon atoms; and
(c) those wherein $R^1$ represents a phenyl or phenoxy group, which may be optionally substituted by a halogen, preferably chlorine, atom;

and especially those such compounds wherein the meanings of symbols $Y^1$, $A^1$ and $R^1$ are in combination as just stated.

Compounds of formula I of particular importance are (R)-2-hydroxy-2,6-dimethyl-11-phenoxyundec-8-trans-en-10-one; [A]
(R)-11-(2-chlorophenoxy)-2-hydroxy-2,6-dimethylundec-8-trans-en-10-one; [B]
(R)-11-(4-chlorophenoxy)-2-hydroxy-2,6-dimethylundec-8-trans-en-10-one; [C]
(R)-2-hydroxy-2,6-dimethyl-10-phenyldec-8-trans-en-10-one; [D]
(R)-10-(4-bromophenyl)-2-hydroxy-2,6-dimethyldec-8-trans-en-10-one; [E]
(R)-2-hydroxy-2,6-dimethyl-13-phenyltridec-8-trans-en-10-one; [F]
(R)-2-hydroxy-2,6-dimethyl-12-phenyldodec-8-trans-en-10-one; [G]
(R)-12-(3-trifluoromethylphenyl)-2-hydroxy-2,6-dimethyldodec-8-trans-en-10-one; [H]
(R)-2-hydroxy-2,6-dimethyl-11-phenylundec-8-trans-en-10-one; [I]
(R)-2-hydroxy-2,6-dimethylpentadec-8-trans-en-10-one; [J]
(R)-2-hydroxy-2,6,11,11-tetramethylpentadec-8-trans-en-10-one; [K]
(R)-12-(4-chlorophenyl)-2-hydroxy-2,6-dimethyldodec-8-trans-en-10-one; [L]
(R)-12-(3-chlorophenyl)-2-hydroxy-2,6-dimethyldodec-8-trans-en-10-one; [M]
(R)-12-(2-chlorophenyl)-2-hydroxy-2,6-dimethyldodec-8-trans-en-10-one; [N]
(R)-11-(3-chlorophenoxy)-2-hydroxy-2,6-dimethylundec-8-trans-en-10-one; [O]
(6R,10RS)-2,6-dimethyl-11-phenoxyundec-8-trans-ene-2,10-diol; [P]
(6R,10RS)-2,6-dimethylpentadec-8-ene-2,10-diol; [Q]
(6R,10RS)-2,6-dimethyl-12-phenyldodec-8-trans-ene-2,10-diol; [R]
(6R,10RS)-2,6-dimethyl-13-phenyltridec-8-trans-ene-2,10-diol; [S]
(6R,10RS)-2,6,11,11-tetramethylpentadec-8-trans-ene-2,10-diol; [T]
(R)-2-hydroxy-2,6-dimethyl-11-phenylthioundec-8-trans-en-10-one; [U]
(R)-2-hydroxy-2,6-dimethyl-13-phenoxytridec-8-trans-en-10-one; [V] and
(6R,10RS)-2,6-dimethyl-11-phenylthioundec-8-trans-ene-2,10-diol.

The letters A to W are assigned to the compounds for easy reference later in the specification, for example in the following Tables.

Compounds of outstanding interest are those identified above by the letters A, B, F, G, K, O, Q, R and T.

The compounds of formula I have utility in several areas, for example they are of use in the field of mammalian reproduction, and they are of use in the control of insects and acarines.

The utility of the compounds of formula I has been demonstrated in, for example, the following laboratory tests:

T.1. Antifertility in hamsters

On the 4th day of pregnancy, hamsters were each injected subcutaneously with an aqueous solution of a compound of formula I (prepared by dissolving the compound in a minimum volume of ethanol and diluting to the appropriate volume with 0.9% w/v saline). On the 7th day of pregnancy the hamsters were killed and their uteri were examined.

Alternatively, the hamsters were dosed on 3 consecutive days (the 3rd, 4th and 5th days of pregnancy) and killed on the 12th day of pregnancy.

The dose required for termination of pregnancy in 50% of the hamsters ($ED_{50}$) was calculated mathematically.

In the compounds of the invention $ED_{50}$ figures were obtained, for example, between about 0.5 and 5 mg/kg animal body weight, for example as shown in Table I below.

TABLE I

| Compound | Day of Examination | ED$_{50}$ (mg/kg) |
| --- | --- | --- |
| A | 12 | about 2 |
| G | 7 | 5 |
| G | 12 | 4 |
| K | 12 | less than 0.5 |
| Q | 12 | 2 |
| R | 12 | 0.5 |
| T | 7 | 2 |

T.2. Stimulation of uterine contraction in rats

Pregnant anaesthetised rats were treated with the compounds of the invention by the intravenous or intravaginal route and the activity of each compound in stimulating uterine contraction was compared with that of a standard compound, the expensive prostaglandin E$_1$ (PGE$_1$), and expressed as a ratio.

In the compounds of the invention, activities relative to PGE$_1$ were found between 100 (more active than PGE$_1$) and 0.015 (less active than PGE$_1$).

For example, compound A was over 100 times as active as PGE$_1$ when administered pervaginally. Results obtained when compounds were administered intravenously are shown in Table II below.

TABLE II

| Compound | Activity (compared with PGE$_1$) |
| --- | --- |
| A | 3.7 |
| B | 1.2 |
| C | 0.32 |
| F | 0.91 |
| G | 0.67 |
| I | 0.09 |
| J | 0.02 |
| K | 0.57 |
| O | 0.91 |
| P | 0.14 |
| Q | 0.05 |
| R | 0.14 |

T.3. Houseflies

Adult houseflies (*Musca domestica* L.) of mixed sex were injected in the dorsal thorax with 1.0 μl of a solution of a test compound in a mixture of acetone and physiological saline (1:1 v/v). Anaesthesia with carbon dioxide was used, and subsequent holding was at 25° C. A source of honey-water was provided. Fly mortality and oviposition were recorded after 24 hours and egg hatching after 48 hours.

Similar, control, experiments were carried out using a mixture of acetone and physiological saline alone.

The results obtained are shown in Table III below.

TABLE III

| Compound | dose (μg/fly) | % mortality | % egg hatch |
| --- | --- | --- | --- |
| G | 0.5 | 60 | no eggs |
|   | 0.1 | 60 | 100 |
| L | 0.5 | 80 | no eggs |
| M | 0.5 | 80 | 0 |
|   | 0.5 | 40 | 0 |
|   | 0.25 | 30 | 100 |
| N | 0.5 | 50 | 100 |
|   | 0.5 | 60 | 100 |
|   | 0.25 | 40 | 100 |
| P | 0.5 | 50 | no eggs |
| Q | 0.5 | 70 | no eggs |
| R | 0.5 | 90 | no eggs |
|   | 0.5 | 40 | 100 |
|   | 0.25 | 40 | 100 |
| S | 0.5 | 30 | few eggs |

TABLE III-continued

| Compound | dose (μg/fly) | % mortality | % egg hatch |
| --- | --- | --- | --- |
|   | 0.5 | 40 | 100 |
|   | 0.25 | 20 | 100 |
| control | 0 | 20 | 50 |
|   | 0 | 10 | 100 |
|   | 0 | 20 | 100 |
|   | 0 | 10 | 100 |

T.4. Ticks

First instar ticks (*Ornithodoros moubata* Murray) were allowed to engorge through a stretched artificial membrane (Parafilm M) on blood at 37° C. and containing a test compound added in a suitable solvent at a rate of 5.0 μg per 0.3 ml blood. Mortality and moulting were observed after 14 days holding at 30° C.

The results are shown in Table IV below.

TABLE IV

| Compound | % mortality | % moulting normally |
| --- | --- | --- |
| G | 0 | 0 |
| L | 0 | 0 |
| M | 0 | 0 |
| N | 0 | 0 |
| P | 0 | 0 |
| Q | 0 | 0 |
| R | 0 | 0 |
| S | 29 | 17 |
| Control | 0 | 25 |
|   | 0 | 41 |

T.5. Mosquitoes

Mosquito larvae (*Aedes aegypti* L.), at the late third or early fourth instar stage, were introduced into water containing a small concentration of a test compound, at 25° C. The water also contained 0.4% v/v acetone which had been employed as the vehicle for the introduction of the test compound. The larvae were fed with dried powdered bovine liver after 2 hours. After 24 hours at 25° C. a mortality count was made, and subsequent metamorphosis and emergence as adults were observed after seven days at 25° C., and compared with controls.

Effective control of the mosquitoes was achieved by, for example, concentrations of test compound of 0.001 to 0.1 parts per million w/v. For example, compound R killed all larvae within 24 hours at 0.08 parts per million w/v, and killed about 50% of larvae within 24 hours at 0.04 parts per million.

T.6. Lucilia pupae

*Lucilia sericata* prepupae (taken from a batch of the insects of which approximately 50% were pupated) in groups of 10 were each treated topically with 1 μl of a solution of a test compound in acetone. Controls were treated with acetone alone. The insects were stored in the dark at 30° C. for 8 days, and then the number of insects which had hatched as normal adult flies, and any other effects, were observed.

The results of three tests are shown below in Table V.

TABLE V

| Test No. | Compound | Dose (μg/prepupa) | Number hatched (out of 10) | Remarks on flies hatched |
| --- | --- | --- | --- | --- |
| 1 | P | 1.0 | 1 | The fly hatched only partially |

TABLE V-continued

| Test No. | Compound | Dose (μg/prepupa) | Number hatched (out of 10) | Remarks on flies hatched |
|---|---|---|---|---|
| | Q | 1.0 | 0 | |
| | Control | 0 | 10 | |
| 2 | Q | 1.0 | 2 | Both flies hatched were abnormal |
| | | 0.8 | 0 | |
| | | 0.6 | 1 | |
| | | 0.4 | 5 | 2 of the 5 flies hatched were abnormal |
| | | 0.2 | 6 | |
| | Control | 0 | 7 | |
| 3 | A | 1.0 | 2 | |
| | Control | 0 | 9 | |

T.7. Toxicity in mammals

The value of the compounds of formula I is enhanced by the fact that they are of negligible toxicity to mammals.

In tests, four female rats and one female dog were each dosed orally with compound A at a rate of 1.0 mg/kg animal body weight. Before administration to the animals the compound was dissolved in a minimum quantity of a 1% w/w solution of Tween 80 emulsifier ("Tween" is a registered Trade Mark) in ethanol, and the resulting solution was diluted with distilled water to a concentration of 0.02% w/w. The animals were observed for a period of two weeks after dosing, during which they suffered no weight loss nor any observable clinical effect.

Compounds of formula I may be prepared by the application or adaptation of known methods. According to a feature of the present invention, compounds of formula I wherein $Y^1$ represents a carbonyl group, $A^1$ and $R^1$ being as hereinbefore defined, are prepared by the reaction of a compound of the formula:

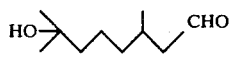

II with a compound of the formula:

$$R^2\text{—CO—}A^1R^1 \qquad\qquad III$$

wherein $A^1$ and $R^1$ are as hereinbefore defined, and $R^2$ represents a group of the formula IV or V:

$$(R^3)_3P\!=\!CH\!- \qquad\qquad IV$$

$$(R^4O)_2P(O)CH_2\!- \qquad\qquad V$$

wherein $R^3$ represents an alkyl group or a phenyl group unsubstituted or substituted by an alkyl group, and advantageously represents a phenyl or n-butyl group, and $R^4$ represents an alkyl group containing from 1 to 4 carbon atoms, preferably a methyl group.

The reaction between compounds of formula II and compounds of formula III wherein $R^2$ represents a group of formula IV ($A^1$, $R^1$ and $R^3$ being as hereinbefore defined) is preferably carried out in the presence of an inert organic solvent and preferably at a temperature between 20° and 100° C., and for example in the presence of tetrahydrofuran as solvent at the reflux temperature of the reaction mixture or in the presence of hexamethylphosphotriamide as solvent at between 95° and 100° C., optionally under an inert atmosphere (e.g. nitrogen).

The reaction between compounds of formula II and compounds of formula III wherein $R^2$ represents a group of formula V ($A^1$, $R^1$ and $R^4$ being as hereinbefore defined) is preferably carried out in the presence of a strong base, for example sodium hydride, preferably in the presence of an inert organic solvent, for example an ether (e.g. tetrahydrofuran), preferably at or near room temperature, e.g. between 10° and 50° C., and optionally under an inert atmosphere (e.g. nitrogen).

According to a further feature of the present invention, compounds of formula I wherein $Y^1$ represents a hydroxymethylene group, $A^1$ and $R^1$ being as hereinbefore defined, are prepared by the reduction of a corresponding compound of formula I wherein $Y^1$ represents a carbonyl group, using means and conditions capable of reducing carbonyl groups to hydroxymethylene groups without affecting carbon-carbon double bonds.

The reduction may be effected by a metal borohydride (e.g. sodium borohydride or potassium borohydride), usually in an aqueous, alcoholic or aqueous alcoholic medium and at a temperature between −40° and +30° C., preferably between −5° and +10° C., optionally in the presence of a base, for example an alkali metal hydroxide (e.g. aqueous sodium hydroxide or aqueous potassium hydroxide) or, especially when potassium borohydride is employed, in aqueous or aqueous alcoholic conditions buffered at a pH of from pH 7 to pH 9, e.g. at pH 8 (e.g. by the addition of aqueous citric acid solution).

Preferably, the reduction can be carried out by means of lithium tri-s-butylborohydride in an inert organic solvent (e.g. tetrahydrofuran), preferably at a temperature between −80° and −50° C., and followed by treatment of the reaction mixture with aqueous alkali (e.g. aqueous sodium hydroxide solution) and aqueous hydrogen peroxide solution.

Compounds of formula III may be prepared by the application or adaptation of known methods.

For example, compounds of formula III wherein $R^2$ represents a group of formula IV, $A^1$, $R^1$ and $R^3$ being as hereinbefore defined, may be prepared by the reaction between a compound of the formula:

$$Q\text{—}CH_2\text{—}CO\text{—}A^1R^1 \qquad\qquad VI$$

(wherein $A^1$ and $R^1$ are as hereinbefore defined and Q represents a bromine or chlorine atom) and an appropriate trialkyl- or triphenylphosphine in a suitable organic solvent (e.g. chloroform), optionally under a nitrogen atmosphere, preferably under anhydrous conditions and at a temperature of from 20° to 100° C., and advantageously at a reflux temperature of the reaction mixture, followed by reaction of the resulting 2-oxoalkylphosphonium halide of the formula:

$$[(R^3)_3PCH_2\text{—}CO\text{—}A^1R^1]^+Q^- \qquad\qquad VII$$

(wherein $A^1$, $R^1$, $R^3$ and Q are as hereinbefore defined) with a base (e.g. aqueous sodium carbonate or ethanolic sodium ethoxide) at ambient temperature.

Alternatively, compounds of formula III wherein $R^2$ represents a group of formula IV, $A^1$ represents a methylene group and $R^1$ represents an optionally substituted phenoxy or phenylthio group, $R^3$ being as hereinbefore defined, may be prepared by the reaction of a phenol or thiophenol of the formula:

$R^5X^1H$                VIII (wherein $R^5X^1$ represents an optionally substituted phenoxy or phenylthio group within the definition of $R^1$, $X^1$ representing an oxygen or sulphur atom) with a compound of the formula:

$(R^3)_3P=CH-CO-CH_2-Q$        IX (wherein $R^3$ and Q are as hereinbefore defined) in the presence of a base (e.g. potassium hydroxide or sodium ethoxide) and in a suitable solvent (e.g. ethanol), preferably at the reflux temperature of the reaction mixture.

As a further alternative, compounds of formula III wherein $R^2$ represents a group of formula IV, $A^1$, $R^1$ and $R^3$ being as hereinbefore defined, may be prepared by the application or adaptation of methods described by Cooke, J. Org. Chem., (1973), 38, 4082.

Compounds of formula III wherein $R^2$ represents a group of formula V, $A^1$, $R^1$ and $R^4$ being as hereinbefore defined, may be prepared by the treatment of a compound of the formula:

$(R^4O)_2P(O)CH_3$        X (wherein $R^4$ is as hereinbefore defined) with butyl lithium at a low temperature, e.g. between $-45°$ and $-60°$ C., and in an inert organic solvent, e.g. a mixture of tetrahydrofuran and hexane, preferably under an inert atmosphere (e.g. nitrogen) and in anhydrous conditions, followed by treatment of the resulting mixture, containing a compound of the formula:

$(R^4O)_2P(O)CH_2Li$        XI (wherein $R^4$ is as hereinbefore defined), with a compound of the formula:

$R^6OOC-A^1R^1$        XII (wherein $A^1$ and $R^1$ are as hereinbefore defined and $R^6$ represents an alkyl, preferably ethyl, group) at a temperature initially between $-70°$ and $-55°$ C. and subsequently rising to room temperature.

As will be readily appreciated by those skilled in the art, the isomeric forms of the compounds of the invention arising from the aforementioned centres of chirality may be separated by the application or adaptation of known methods, for example diastereoisomeric forms may be separated by chromatography using selective adsorption from solution or from the vapour phase onto suitable adsorbents.

By the term "known methods" as used in this specification is meant methods heretofore used or described in the literature.

The following Examples illustrate the preparation of the tertiary alcohols of the present invention, and the Reference Examples thereafter illustrate the preparation of intermediates.

EXAMPLE 1

Compounds A, B, C, D, E and F

A mixture of (R)-hydroxycitronellal [i.e. (R)-7-hydroxy-3,7-dimethyloctanal] (1.72 g) and 2-oxo-3-phenoxypropylidenetriphenylphosphorane (4.1 g) in hexamethylphosphotriamide (40 ml) was heated on the steam bath under dry nitrogen for 70 hours. The mixture was then poured into water (100 ml) and extracted with diethyl ether. The ethereal solution was washed with water, dried over magnesium sulphate and concentrated to low bulk. The triphenylphosphine oxide which separated was removed by filtration, and the filtrate was concentrated further to give a mixture (4.4 g) of crude product and triphenylphosphine oxide. A portion (0.5 g) of this residue was purified by preparative thin layer chromatography on silica gel, using a mixture of ethyl acetate, cyclohexane, and 90% w/w formic acid (200:200:5 by volume) as eluant, to give (R)-2-hydroxy-2,6-dimethyl-11-phenoxyundec-8-trans-en-10-one (86 mg) in the form of a pale yellow oil. [elemental analysis: C, 72.9; H, 9.4%. $C_{19}H_{28}O_3:0.5H_2O$ requires C, 72.8; H, 9.3%. $\nu_{max}$ 985, 1380, 1600, 1625, and 3400 cm$^{-1}$. NMR (10% w/v solution in deuterochloroform): multiplets at 6.8–7.5δ, 1.15–2.4δ, doublets at 6.4δ (J=16 cycles/second) and 0.9δ (J=6 cycles/second), singlet at 4.7δ].

By proceeding in a similar manner but replacing the 2-oxo-3-phenoxypropylidenetriphenylphosphorane, used as a starting material, by the appropriate quantities of 3-(2-chlorophenoxy)-2-oxopropylidenetriphenylphosphorane, 3-(4-chlorophenoxy)-2-oxopropylidenetriphenylphosphorane, benzoylmethylenetriphenylphosphorane, 4-bromobenzoylmethylenetriphenylphosphorane, and 4-phenylbutyrylmethylenetriphenylphosphorane, respectively, there were prepared (R)-11-(2-chlorophenoxy)-2-hydroxy-2,6-dimethylundec-8-trans-en-10-one [elemental analysis: C, 67.3; H, 8.2%. $C_{19}H_{27}ClO_3$ requires C, 67.3; H, 8.0%. $\nu_{max}$ 985, 1380, 1590, 1630 and 3400 cm$^{-1}$. NMR (approximately 10% w/v solution in deuterochloroform): multiplets at 6.7–7.6δ, 1.15–2.4δ, doublets at 6.5δ (J=16 cycles/second) and 0.9δ (J=6 cycles/second), singlet at 4.75δ];

(R)-11-(4-chlorophenoxy)-2-hydroxy-2,6-dimethylundec-8-trans-en-10-one [elemental analysis: C, 67.1; H, 8.3%. $C_{19}H_{27}ClO_3$ requires C, 67.3; H, 8.0%. $\nu_{max}$ 985, 1380, 1595, 1630 and 3400 cm$^{-1}$. NMR (approximately 10% w/v solution in deuterochloroform): multiplets at 6.7–7.4δ, 1.15–2.4δ, doublets at 6.35δ (J=15 cycles/second) and 0.9δ (J=6 cycles/second), singlet at 4.7δ];

(R)-2-hydroxy-2,6-dimethyl-10-phenyldec-8-trans-en-10-one [elemental analysis: C, 78.4; H, 9.2%. $C_{18}H_{26}O_2$ requires C, 78.8; H, 9.55%. $\nu_{max}$ 980, 1380, 1595, 1620 and 3400 cm$^{-1}$. $\lambda_{max}$ 253 nm, $\epsilon_{max}$ 17,300; $\lambda_{max}$ 203 nm, $\epsilon_{max}$ >16,000. NMR (approximately 10% w/v solution in deuterochloroform): multiplets at 7.8–8.2δ 6.9–7.8δ, 2.0–2.5δ and 1.1–2.0δ, doublet at 0.95δ (J=6 cycles/second)];

(R)-10-(4-bromophenyl)-2-hydroxy-2,6-dimethyldec-8-trans-en-10-one [elemental analysis: C, 60.3; H, 6.95%. $C_{18}H_{25}BrO_2$: 0.25 $H_2O$ requires C, 60.2; H, 7.2%. $\nu_{max}$ 980, 1380, 1585, 1620 and 3400 cm$^{-1}$. $\lambda_{max}$ 267 nm, $\epsilon_{max}$ 22400. NMR (approximately 10% w/v solution in deuterochloroform): multiplets at 6.9–8.0δ, 1.2–2.45δ, doublet at 0.95δ, (J=5.5 cycles/second)]; and (R)-2-hydroxy-2,6-dimethyl-13-phenyltridec-8-tans-en-10-one [elemental analysis: C, 79.6; H, 10.6%. $C_{21}H_{32}O_2$ requires C, 79.7; H, 10.2%. $\nu_{max}$ 980, 1380, 1630 and 3400. NMR (approximately 10% w/v solution in deuterochloroform): multiplets at 2.3–2.9δ, 1.1–2.3δ, doublet of triplets at 6.8δ (J=15.5 and 7 cycles/second), doublets at 6.0δ (J=15.5 cycles/second) and 0.9δ (J=5.5 cycles/second)].

EXAMPLE 2

Compounds G, H, I, J, K, L, M and N

A solution of dimethyl 2-oxo-4-phenylbutylphosphonate (1.5 g) in anhydrous tetrahydrofuran (20 ml) was added to a stirred suspension of sodium hydride (0.14 g) in anhydrous tetrahydrofuran (20 ml) in an atmosphere of nitrogen. The mixture was stirred at room temperature for 24 hours and was then treated with a solution of (R)-hydroxycitronellal (1.0 g) in anhydrous tetrahydrofuran (15 ml) and stirred for a further 3 hours in an atmosphere of nitrogen. The pH of the solution was adjusted to 4 by the addition of glacial acetic acid, the solvent was removed in vacuo, and the residue was extracted with diethyl ether. The ethereal solution was washed with water, with aqueous sodium bicarbonate solution (10% w/v), and then with water, dried over magnesium sulphate, and evaporated to leave a residue (1.9 g), a portion of which (0.3 g) was purified by preparative thin layer chromatography on silica gel, using a mixture of ethyl acetate, cyclohexane and 90% w/w formic acid (200:200:5 by volume) as eluant, to give (R)-2-hydroxy-2,6-dimethyl-12-phenyldodec-8-trans-en-10-one (125 mg) in the form of a very pale yellow oil. [elemental analysis: C, 79.6; H, 10.1%. $C_{20}H_{30}O_2$ requires C, 79.4; H, 10.0%. $\nu_{max}$ 980, 1375, 1625 and 3450 cm$^{-1}$. NMR (approximately 10% w/v solution in deuterochloroform): multiplets at 1.15–2.3$\delta$ and 0.7–1.0$\delta$, doublet of triplets at 6.8$\delta$ (J=16 and 6 cycles/second), doublet at 6.05$\delta$ (J=16 cycles/second), singlets at 7.2$\delta$ and 2.85$\delta$].

By proceeding in a similar manner but replacing the dimethyl 2-oxo-4-phenylbutylphosphonate, used as a starting material, by the appropriate quantities of dimethyl 4-(3-trifluoromethylphenyl)-2-oxobutylphosphonate, dimethyl 2-oxo-3-phenylpropylphosphonate, dimethyl 2-oxoheptylphosphonate, dimethyl 3,3-dimethyl-2-oxoheptylphosphonate, dimethyl 4-(4-chlorophenyl)-2-oxobutylphosphonate, dimethyl 4-(3-chlorophenyl)-2-oxobutylphosphonate, and dimethyl 4-(2-chlorophenyl)-2-oxobutylphosphonate, respectively, there were prepared (R)-12-(3-trifluoromethylphenyl)-2-hydroxy-2,6-dimethyldodec-8-trans-en-10-one [elemental analysis: C, 66.9; H, 7.8%. $C_{21}H_{29}F_3O_2$ requires C, 67.3; H, 7.9: $\lambda_{max}$ 980, 1125, 1165, 1330, 1380, 1625 and 3450 cm$^{-1}$. NMR (approximately 10% w/v solution in deuterochloroform): multiplets at 6.55–7.25$\delta$, 2.65–3.15$\delta$, 1.15–2.3$\delta$, doublets at 6.1$\delta$ (J=16 cycles/second) and 0.9$\delta$ (J=5.5 cycles/second), singlet at 7.4$\delta$];

(R)-2-hydroxy-2,6-dimethyl-11-phenylundec-8-trans-en-10-one [elemental analysis: C, 78.5; H, 9.4$\delta$. $C_{19}H_{28}O_2$.0.1$H_2O$ requires C, 78.6; H, 9.8%. $\nu_{max}$ 980, 1625 and 3400 cm$^{-1}$. NMR (approximately 10% w/v solution in deuterochloroform): multiplets at 1.05–2.35$\delta$, doublet of triplets at 6.9$\delta$ (J=16 and 7.5 cycles/second), doublets at 6.13$\delta$ (J=15.5 cycles/second) and 0.9$\delta$ (J=6 cycles/second), singlets at 7.3$\delta$ and 3.8$\delta$];

(R)-2-hydroxy-2,6-dimethylpentadec-8-trans-en-10-one [elemental analysis: C, 76.0; H, 12.1%. $C_{17}H_{32}O_2$ requires C, 76.1; H, 12.0%. $\nu_{max}$ 980, 1165, 1378, 1625 and 3425 cm$^{-1}$. $\lambda_{max}$ 225 nm, $\epsilon_{max}$ 14500. NMR (approximately 10% w/v solution in deuterochloroform): multiplets at 6.5–7.1$\delta$, 0.75–1.1$\delta$, 1.1–1.95$\delta$, 1.95–2.4$\delta$, and 2.4–2.7$\delta$, doublet at 6.08$\delta$ (J=16 cycles/second)];

(R)-2-hydroxy-2,6,11,11-tetramethylpentadec-8-trans-en-10-one [elemental analysis: C, 77.0; H, 12.4%. $C_{19}H_{36}O_2$ requires C, 77.0; H, 12.2%. $\nu_{max}$ 980, 1155, 1375, 1622 and 3420 cm$^{-1}$. NMR (approximately 10% w/v solution in deuterochloroform): multiplets at 6.65–7.1$\delta$, 1.0–1.9$\delta$ and 1.9–2.3$\delta$, doublets at 6.45$\delta$ (J=15.5 cycles/second) and 0.9$\delta$ (J=5 cycles/second)];

(R)-12-(4-chlorophenyl)-2-hydroxy-2,6-dimethyldodec-8-trans-en-10-one [elemental analysis: C, 71.0; H, 8.8%. $C_{20}H_{29}ClO_2$ requires C, 71.3; H, 8.7%. $\nu_{max}$ 985, 1380, 1635 and 3450 cm$^{-1}$. NMR (approximately 10% w/v solution in deuterochloroform): multiplets at 7.15–7.35$\delta$, 6.55–7.15$\delta$, 1.15–2.4$\delta$, doublets at 6.05$\delta$ (J=16 cycles/second) and 0.9$\delta$ (J=6 cycles/second), singlet at 2.8$\delta$];

(R)-12-(3-chlorophenyl)-2-hydroxy-2,6-dimethyldodec-8-trans-en-10-one [elemental analysis: C, 71.1; H, 8.8%. $C_{20}H_{29}ClO_2$ requires C, 71.3; H, 8.7%. $\nu_{max}$ 985, 1385, 1635 and 3450 cm$^{-1}$. NMR (approximately 10% w/v solution in deuterochloroform): multiplets at 7.0–7.35$\delta$, 2.8–2.95$\delta$, 1.1–2.3$\delta$, doublet of triplets at 6.85$\delta$ (J=16 cycles/second and 7 cycles/second), doublets at 6.05$\delta$ (J=16 cycles/second) and 0.88$\delta$ (J=6 cycles/second)]; and (R)-12-(2-chlorophenyl)-2-hydroxy-2,6-dimethyldodec-8-trans-en-10-one [elemental analysis: C, 71.4; H, 8.7%. $C_{20}H_{29}ClO_2$ requires C, 71.3; H, 8.7%. $\nu_{max}$ 985, 1380, 1630 and 3450 cm$^{-1}$. NMR (approximately 10% w/v solution in deuterochloroform): multiplets at 7.0–7.5$\delta$, 2.65–3.3$\delta$ and 1.05–2.5$\delta$, doublet of triplets at 6.9$\delta$ (J=16 cycles/second and 7.5 cycles/second), doublets at 6.1$\delta$ (J=16 cycles/second) and 0.9$\delta$; (J=6 cycles/second)].

EXAMPLE 3

Compounds O and C

A solution of dimethyl 3-(3-chlorophenoxy)-2-oxopropylphosphonate (2.4 g) in anhydrous tetrahydrofuran (15 ml) was added dropwise to a stirred suspension of sodium hydride (0.36 g) in anhydrous tetrahydrofuran (20 ml) in an atmosphere of nitrogen. The temperature rose to 43° C., and the mixture was maintained at this temperature by external heating for 30 minutes. The mixture was then treated dropwise with a solution of (R)-hydroxycitronellal (1.2 g) in anhydrous tetrahydrofuran (10 ml) and stirred at between 43° and 47° C. for a further 3 hours.

The solvent was removed in vacuo, and the residue was extracted with diethyl ether. The ethereal solution was washed with water, with dilute hydrochloric acid (2 N), and with water and was then dried over magnesium sulphate and evaporated to leave a residue (0.95 g) a portion of which (0.5 g) was purified by preparative thin layer chromatography on silica gel, using as eluant a mixture of ethyl acetate, cyclohexane and 90% w/w formic acid (200:200:5 by volume), to give (R)-11-(3-chlorophenoxy)-2-hydroxy-2,6-dimethylundec-8-trans-en-10-one (51 mg) in the form of a pale yellow oil. [elemental analysis: C, 67.1; H, 8.1%. $C_{19}H_{27}ClO_3$ requires C, 67.3; H, 8.0%. $\nu_{max}$ 985, 1380, 1600, 1630 and 3450 cm$^{-1}$. NMR (approximately 10% w/v solution in deuterochloroform): multiplets at 6.7–7.4$\delta$, 2.0–2.4$\delta$ and 1.15–2.0$\delta$, doublets at 6.4$\delta$ (J=16.5 cycles/second) and 0.9$\delta$ (J=6 cycles/second)].

by proceeding in a similar manner but replacing the dimethyl 3-(3-chlorophenoxy)-2-oxopropylphosphonate, used as a starting material, by the appropriate quantity of dimethyl 3-(4-chlorophenoxy)-2-oxopropylphosphonate, there was prepared (R)-11-(4-chlorophenoxy)-2-hydroxy-2,6-dimethylundec-8-trans-en-10-one [elemental analysis C, 67.1; H, 8.4%. $C_{19}H_{27}ClO_3$ requires C, 67.3; H, 8.0%. $\nu_{max}$ 980, 1380, 1595, 1630 and 3450 cm$^{-1}$. NMR (approximately 10% w/v solution in deuterochloroform): multiplets at 6.65–7.4δ, 1.05–2.5δ, doublets at 6.35δ (J=16 cycles/second) and 0.9δ (J=6.5 cycles/second), singlet at 4.68δ].

EXAMPLE 4

Compounds P, Q, R and S

A solution of crude (R)-2-hydroxy-2,6-dimethyl-11-phenoxyundec-8-trans-en-10-one (1.0 g) in anhydrous tetrahydrofuran (10 ml) was added dropwise to a stirred solution of lithium tri-s-butylborohydride (0.62 g) in anhydrous tetrahydrofuran (3.26 ml) at −78° C. under dry nitrogen, and then the solution was stirred at −78° C. for 30 minutes and at ambient temperature for 3 hours. The mixture was hydrolysed and oxidised by the dropwise addition of aqueous sodium hydroxide solution (3 N; 2.4 ml) and aqueous hydrogen peroxide solution (100 volume; 1.49 ml), cooling in an ice bath, and then it was stirred at ambient temperature for one hour. The mixture was then diluted with diethyl ether and water, and the organic layer was separated and washed with water, with dilute hydrochloric acid (2 N), and with water, then dried over magnesium sulphate and evaporated, to give a residue (1.4 g). A portion (0.5 g) of this material was purified by preparative thin layer chromatography on silica gel, using a mixture of ethyl acetate, cyclohexane and 90% w/w formic acid (40:40:1 by volume) as eluant, to give (6R,10RS)-2,6-dimethyl-11-phenoxyundec-8-trans-ene-2,10-diol (94 mg) [elemental analysis: C, 74.1; H, 10.1%. $C_{19}H_{30}O_3$ requires C, 74.5; H, 9.9%. $\nu_{max}$ 975, 1000, 1600 and 3390 cm$^{-1}$. NMR (approximately 10% w/v solution in deuterochloroform): multiplets at 6.85–7.5δ, 4.3–4.6δ, 3.8–4.0δ and 1.1–1.85δ, triplet at 5.7δ (J=4 cycles/second), doublet at 0.88δ (J=5 cycles/second), broad singlet at 2.0δ].

By proceeding in a similar manner but replacing the (R)-2-hydroxy-2,6-dimethyl-11-phenoxyundec-8-trans-en-10-one by the appropriate quantities of (R)-2-hydroxy-2,6-dimethylpentadec-8-trans-en-10-one, (R)-2-hydroxy-2,6-dimethyl-12-phenyldodec-8-trans-en-10-one and (R)-2-hydroxy-2,6-dimethyl-13-phenyltridec-8-trans-en-10-one, respectively, there were prepared (6R,10RS)-2,6-dimethylpentadec-8-trans-ene-2,10-diol [elemental analysis: C, 75.0; H, 12.6%. $C_{17}H_{34}O_2 \cdot 0.1H_2O$ requires C, 75.0; H, 12.7%. $\nu_{max}$ 970, 3380 cm$^{-1}$. NMR (approximately 10% w/v solution in deuterochloroform); multiplets at 5.2–5.9δ, 3.9–4.2δ, 1.75–2.1δ, 1.15–1.75δ, 0.75–1.1δ]; (6R,10RS)-2,6-dimethyl-12-phenyldodec-8-trans-ene-2,10-diol [elemental analysis: C, 79.2; H, 10.9%. $C_{20}H_{32}O_2$ requires C, 78.9; H, 10.6%. $\nu_{max}$ 970, 990, 1605 and 3400 cm$^{-1}$. NMR (approximately 10% w/v solution in deuterochloroform): multiplets at 5.25–5.95δ, 3.9–4.25δ, 2.5–2.85δ, 1.1–2.5δ, doublet at 0.9δ (J=5.5 cycles/second), singlet at 7.2δ]; and (6R,10RS)-2,6-dimethyl-13-phenyltridec-8-trans-ene-2,10-diol [elemental analysis: C, 79.2; H, 10.8%. $C_{21}H_{34}O_2$ requires C, 79.2; H, 10.8%. $\nu_{max}$ 978, 1380, 1608 and 3380 cm$^{-1}$. NMR (approximately 10% w/v solution in deuterochloroform): multiplets at 5.15–5.9δ, 3.85–4.25δ, 2.25–2.8δ and 1.05–2.25δ, doublet at 0.85δ (J=5.5 cycles/second), singlet at 7.25δ].

EXAMPLE 5

Compound T

A solution of (R)-2-hydroxy-2,6,11,11-tetramethylpentadec-8-trans-en-10-one (0.5 g) in methanol (15 ml) was added to aqueous sodium citrate solution (50 ml; 2% w/v), maintaining the temperature at −5° C. The stirred solution was then treated portionwise with potassium borohydride (2.27 g) during 20 minutes, still maintaining the temperature at −5° C., and maintaining the mixture at pH 8 by means of the addition of small quantities of aqueous citric acid solution (10% w/v). Further quantities of methanol were added occasionally, so as to keep the organic material in solution.

The solution was stirred for a further period of one hour at the temperature of −5° C. and at pH 8. The solution was then treated with acetone (20 ml) and then saturated with sodium chloride and extracted with diethyl ether. The ethereal extract was washed with saturated aqueous sodium bicarbonate solution, with dilute hydrochloric acid (2 N), and with water, and was then dried over magnesium sulphate and evaporated. The residue was purified by preparative thin layer chromatography on silica gel, using a mixture of ethyl acetate, cyclohexane and 90% w/w formic acid (200:200:5 by volume) as eluant, to give (6R,10RS)-2,6,11,11-tetramethylpentadec-8-trans-ene-2,10-diol (18 mg) in the form of a pale yellow oil. [elemental analysis: C, 76.5; H, 12.7%; $C_{19}H_{38}O_2$ requires C, 76.45; H, 12.8%. $\nu_{max}$ 980, 1380 and 3400 cm$^{-1}$. NMR (approximately 10% w/v solution in deuterochloroform): multiplets at 5.2–5.8δ, 3.68–3.85δ, 1.1–2.1δ and 0.8–1.1δ].

EXAMPLE 6

Compounds U and V

A solution of (R)-hydroxycitronellal (1.72 g) and 2-oxo-3-phenylthiopropylidenetriphenylphosphorane (4.26 g) in anhydrous tetrahydrofuran (50 ml) was heated at reflux under dry nitrogen for 72 hours, and was then concentrated to dryness under reduced pressure. Diethyl ether was added to the residue and the mixture was stored at 0° C. The solid which then separated was filtered off, and the filtrate was concentrated to dryness, to give a crude mixture (3.8 g) of (R)-2-hydroxy-2,6-dimethyl-11-phenylthioundec-8-trans-en-10-one and triphenylphosphine oxide. A portion (200 mg) of this residue was purified by preparative thin layer chromatography on silica gel, using a mixture of diethyl ether, ethyl acetate and n-hexane (2:1:1 by volume) as eluant, to give (R)-2-hydroxy-2,6-dimethyl-11-phenylthioundec-8-trans-en-10-one (56 mg) in the form of a yellow oil [elemental analysis: C, 70.7; H, 9.0%; $C_{19}H_{28}O_2S \cdot 0.1H_2O$ requires C, 70.8; H, 8.8%. $\nu_{max}$ 980, 1380, 1590, 1630 and 3400 cm$^{-1}$. NMR (10% w/v solution in deuterochloroform): multiplets at 7.1–7.55δ, 6.55–7.1δ, 2.0–2.4δ, 1.1–2.0δ, doublets at 6.3δ (J=15.5 cycles/second) and 0.9δ (J=6 cycles/second), singlet at 3.8δ].

By proceeding in a similar manner but replacing the 2-oxo-3-phenylthiopropylidenetriphenylphosphorane used as starting material by the appropriate quantity of 2-oxo-5-phenoxypentylidenetriphenylphosphorane, and by using a mixture of ethyl acetate, cyclohexane and 90% w/v formic acid (200:200:5 by volume) as the eluant for the preparative thin-layer chromatography, there was prepared (R)-2-hydroxy-2,6-dimethyl-13-phenoxytridec-8-trans-en-10-one [elemental analysis: C, 76.0; H, 9.6%, $C_{21}H_{32}O_3$ requires C, 75.9; H, 9.7%. $\nu_{max}$ 985, 1385, 1605, 1630 and 3400 cm$^{-1}$. NMR (approximately 10% w/v solution in deuterochloroform); multiplets 6.6–7.5$\delta$, 1.15–2.45$\delta$, triplets at 4.0$\delta$ (J=6 cycles/second) and 2.8$\delta$ (J=6.5 cycles/second), doublets at 6.1$\delta$ (J=16 cycles/second) and 0.9$\delta$ (J=6 cycles/second)].

EXAMPLE 7

Compound W

A solution of crude (R)-2-hydroxy-2,6-dimethyl-11-phenylthioundec-8-trans-en-10-one (1.0 g) in anhydrous tetrahydrofuran (10 ml) was added dropwise to a stirred solution of lithium tri-s-butylborohydride (0.5 g) in anhydrous tetrahydrofuran (2.6 ml) at $-78°$ under dry nitrogen, and the solution was stirred at $-78°$ C. for 30 minutes and then at ambient temperature for 3 hours. The mixture was then treated, dropwise, with aqueous sodium hydroxide solution (3 N; 1.92 ml) and aqueous hydrogen peroxide solution (100 volume; 1.21 ml), cooling in an ice-bath, and then it was stirred at ambient temperature for one hour. The mixture was diluted with diethyl ether and water and the organic layer was separated and washed with water, then with dilute hydrochloric acid (2 N), and then again with water, and was dried over magnesium sulphate and evaporated to give a residue (1.0 g). A portion (300 mg) of this residue was purified by preparative thin layer chromatography on silica gel using a mixture of diethyl ether, ethyl acetate and n-hexane (2:1:1 by volume) as eluant, to give (6R,10RS)-2,6-dimethyl-11-phenylthioundec-8-trans-ene-2,10-diol (57 mg) in the form of a yellow oil [elemental analysis: C, 70.4; H, 9.6%. $C_{19}H_{30}O_2S$ requires C, 70.8; H, 9.4%. $\nu_{max}$ 970, 1000, 1590 and 3400 cm$^{-1}$. NMR (approximately 10% w/v solution in deuterochloroform): multiplets at 7.1–7.55$\delta$, 5.15–5.9$\delta$, 3.95–4.35$\delta$, 2.8–3.18$\delta$, 1.05–2.4$\delta$, doublet at 0.9$\delta$ (J=5.5 cycles/second)].

REFERENCE EXAMPLE 1

3-Bromo-2-oxopropylidenetriphenylphosphorane (8.0 g) was added to a solution of o-chlorophenol (3.8 g) and potassium hydroxide (1.56 g) in anhydrous ethanol (60 ml), and the resulting mixture was heated at reflux for 2 hours and was then poured into water (200 ml). The mixture was extracted with methylene chloride and the extract was washed with dilute aqueous sodium hydroxide solution (2 N) and with water, dried over magnesium sulphate, and evaporated. The residual solid was recrystallised from a mixture of petroleum ether (b.p. 60°–80° C.) and ethyl acetate, to give 3-(2-chlorophenoxy)-2-oxopropylidenetriphenylphosphorane (4.5 g), m.p. 102°–104° C. A further recrystallisation from a similar solvent gave a purer sample, m.p. 107°–109° C. [elemental analysis: C, 73.1; H, 5.3; P, 7.0%. $C_{27}H_{22}ClO_2P$ requires C, 72.9; H, 5.0; P, 6.95%. $\nu_{max}$ 715, 750, 1110, 1405, 1440, 1485 and 1550 cm$^{-1}$].

By proceeding in a similar manner but replacing the o-chlorophenol by the appropriate quantity of p-chlorophenol, there was prepared 3-(4-chlorophenoxy)2-oxopropylidenetriphenylphosphorane, m.p. 120°–123° C. [elemental analysis: P, 7.4%. $C_{27}H_{22}ClO_2P$ requires P, 6.95%. $\nu_{max}$ 715, 745, 825, 1105, 1405, 1440, 1490 and 1545 cm$^{-1}$].

REFERENCE EXAMPLE 2

A solution of n-butyl lithium (5.88 g) in hexane (48 ml) and anhydrous diethyl ether (70 ml) was added to a stirred solution of dimethyl methylphosphonate (11.4 g) in anhydrous tetrahydrofuran (50 ml) at $-50°$ C. in an atmosphere of nitrogen during 20 minutes. The solution was stirred for a further 15 minutes at $-60°$ C., and was then treated with a solution of ethyl 3-(3-trifluoromethylphenyl)-propionate (11.3 g) in anhydrous tetrahydrofuran (20 ml) during 10 minutes at $-60°$ C. The solution was stirred at $-60°$ C. for 90 minutes and then at ambient temperature for 2 hours. The solution was then treated with acetic acid (10 ml) and the solvents were evaporated off under reduced pressure. Water (75 ml) was added to the resulting gelatinous residue and the mixture was extracted with diethyl ether. The ethereal solution was washed with water, with aqueous sodium bicarbonate solution (10% w/v), and with water, dried over magnesium sulphate, and evaporated. The residue was distilled to give dimethyl 4-(3-trifluoromethylphenyl)-2-oxobutylphosphonate (7.4 g) in the form of a colourless oil, b.p. 157°–159° C./0.2 mm Hg. [elemental analysis: C, 48.3; H, 5.1; P, 9.8%. $C_{13}H_{16}F_3O_4P$ requires C, 48.15; H, 5.0; P, 9.55%. $\nu_{max}$ 1035, 1125, 1165, 1265, 1330, 1555 and 1720 cm$^{-1}$].

By proceeding in a similar manner but replacing the ethyl 3-(3-trifluoromethylphenyl)propionate used as a starting material by the appropriate quantities of ethyl 3-(4-chlorophenyl)propionate, ethyl 3-(3-chlorophenyl)propionate and ethyl 3-(2-chlorophenyl)propionate, respectively, there were prepared dimethyl 4-(4-chlorophenyl)-2-oxobutylphosphonate, b.p. 180°–184° C./0.2 mm Hg. [elemental analysis: C, 49.8; H, 5.7; p 10.5%. $C_{12}H_{16}ClO_4P$ requires C, 49.6; H. 5.55; P, 10.7%. $\nu_{max}$ 820, 1040, 1270, 1495 and 1720 cm$^{-1}$]; dimethyl 4-(3-chlorophenyl)-2-oxobutylphosphonate b.p. 178°–184° C./0.15 mm Hg. [elemental analysis: C, 49.2; H, 5.8; P, 10.5%. $C_{12}H_{16}ClO_4P$ requires C, 49.6; H 5.55; P, 10.7%. $\nu_{max}$ 815, 1035, 1265, 1483 and 1720 cm$^{-1}$]; and dimethyl 4-(2-chlorophenyl)-2-oxobutylphosphonate, b.p. 178°–188° C./0.15 mm Hg. [elemental analysis: C, 49.8; H, 5.7; P, 10.8%. $C_{12}H_{16}ClO_4P$ requires C, 49.6; H, 5.55; P, 10.8%. $\nu_{max}$ 760, 1040, 1270, 1480 and 1720 cm$^{-1}$].

REFERENCE EXAMPLE 3

A solution of 3-(3-trifluoromethylphenyl)propionic acid (13.6 g) in anhydrous ethanol (25 ml) containing concentrated sulphuric acid (1.5 ml) was heated at reflux for 24 hours and was then poured into water (100 ml). The mixture was extracted with diethyl ether and the ethereal extract was washed with water, with aqueous sodium carbonate solution (2 N), and with water, then dried over magnesium sulphate and evaporated. The resulting residue was distilled, to give ethyl 3-(3-trifluoromethylphenyl)propionate (11.5 g) in the form of a colourless oil, b.p. 133°–135° C./17 mm Hg. [elemental analysis: C, 58.6; H, 5.2%. $C_{12}H_{13}F_3O_2$ requires C, 58.5; H, 5.3%. $\nu_{max}$ 1125, 1170, 1330 and 1740 cm$^{-1}$].

REFERENCE EXAMPLE 4

A solution of n-butyl lithium (16.0 g) in hexane (160 ml) was added to a stirred solution of dimethyl methylphosphonate (26.9 g) in anhydrous tetrahydrofuran (150 ml) at $-60°$ C. in an atmosphere of nitrogen during 20 minutes. The solution was maintained at $-60°$ C. for a further period of 10 minutes and was then treated with a solution of ethyl 3-chlorophenoxyacetate (23.4 g) in anhydrous tetrahydrofuran (50 ml) at −60° C. during a further period of 10 minutes. This solution was stirred at −60° C. for 90 minutes and then stirred at ambient temperature for 2 hours. The solution was treated with acetic acid (21 ml) and the solvents were evaporated under reduced pressure. Water (60 ml) was added to the residue and the mixture was extracted with diethyl ether. The ethereal solution was washed with water, with aqueous sodium bicarbonate solution (10% w/v) and with water, dried over magnesium sulphate, and evaporated. The resulting residue was left to stand at ambient temperature overnight. The resulting colourless crystals were filtered off, washed with a small volume of diethyl ether, and recrystallised from a mixture of petroleum ether (b.p. 40°-60° C.) and toluene, to give dimethyl 3-(3-chlorophenoxy)-2-oxopropylphosphonate (18.6 g) in the form of colourless needles, m.p. 78°-79° C. [elemental analysis: C, 44.9; H, 5.1; P, 10.7%. $C_{11}H_{14}ClO_5P$ requires C, 45.1; H, 4.8; P, 10.6%. $\nu_{max}$ 825, 865, 1030, 1160, 1270, 1335, 1600 and 1735 cm$^{-1}$].

REFERENCE EXAMPLE 5

By proceeding as hereinbefore described in Reference Example 2 but replacing the ethyl 3-(3-trifluoromethylphenyl)propionate, used as a starting material, by the appropriate quantity of ethyl p-chlorophenoxyacetate, there was prepared dimethyl 3-(4-chlorophenoxy)-2-oxopropylphosphonate, b.p. 192°-196° C./0.4 mm Hg. [elemental analysis: C, 44.8; H, 4.9; Cl, 11.9%. $C_{11}H_{14}ClO_5P$ requires C, 45.1; H, 4.8; Cl, 12.1%. $\nu_{max}$ 830, 1035, 1245, 1490, 1595, 1735 cm$^{-1}$].

REFERENCE EXAMPLE 6

3-Bromo-2-oxopropylidenetriphenylphosphorane (17.85 g) was added to a solution of thiophenol (5.22 g; 4.86 ml) in anhydrous ethanol (70 ml) containing sodium (1.09 g). The mixture was heated at reflux for 150 minutes and was then poured into a mixture of ice and water (250 ml). The mixture was then extracted with dichloromethane and the extract was washed with dilute aqueous sodium hydroxide solution (2 N) and then with water, and was dried over magnesium sulphate. Evaporation of the solvent gave a residual oil which was triturated with petroleum ether (b.p. 40°-60° C.), and the resulting crude solid was recrystallised from a mixture of toluene and petroleum ether (b.p. 60°-80° C.) to give 2-oxo-3-phenylthiopropylidenetriphenylphosphorane (14.2 g) in the form of cream prisms, m.p. 132°-134° C. [elemental analysis: C, 76.4; H, 5.3; P, 7.3; S, 7.7%. $C_{27}H_{23}OPS$ requires C, 76.0; H, 5.4; P, 7.3; S, 7.5%. $\nu_{max}$ 715, 740, 750, 1110, 1385, 1440, 1485 and 1550 cm$^{-1}$].

REFERENCE EXAMPLE 7

A solution of n-butyl lithium (2.69 g) in hexane (26.25 ml) was added dropwise to a stirred solution of 2-oxopropylidenetriphenylphosphorane (12.73 g) in anhydrous tetrahydrofuran (400 ml) at −65° C. in an atmosphere of dry nitrogen. The red solution was stirred at −65° C. for a further 15 minutes and was then treated with a solution of 2-phenoxyethyl bromide (8.04 g) in anhydrous tetrahydrofuran (40 ml). The mixture was stirred at 0° C. for one hour and then at ambient temperature for 2 hours, and was poured into water and extracted with diethyl ether. The organic solution was washed with water then dried over magnesium sulphate. Evaporation of the solution gave a yellow gum which slowly hardened on prolonged storage after trituration with diethyl ether to give crude 2-oxo-5-phenoxypentylidenetriphenylphosphorane (8.0 g), m.p. 83°-89° C. [elemental analysis: P, 7.4%; $C_{29}H_{27}O_2P$ requires P, 7.1%. $\nu_{max}$ 715, 755, 1110, 1400, 1445, 1490 and 1555 cm$^{-1}$. NMR (approximately 10% w/v solution in deuterochloroform): multiplets at 6.7-7.9δ and 1.8-2.7δ, triplet at 4.0δ (J=6 cycles/second)].

The compounds of formula I are useful in modifying, qualitatively or quantitatively, or synchronising various functions of female mammalian reproductive systems.

The compounds of formula I are useful in the control of insects and acarines, for example they are effective against Hemiptera, for example Lygaeidae, Miridae and Pyrrhocoridae; against Lepidoptera, for example Pyralidae, Noctuidae and Gelechiidae; against Coleoptera, for example Tenebrionidae, Chrysomelidae and Dermestidae; against Diptera, for example mosquitoes and flies; and Homoptera, for example aphids; and other insects and acarines.

The compounds of formula I may be used to control insects and acarines which are injurious to growing crops, stored products including foodstuffs, household goods, timber, property, farm and domestic or other desirable animals, and humans, to control insects and acarines which spread or act as vectors of disease to man, to animals, or to plants, and to control insects which are aesthetically undesirable.

Suitable means of applying the compounds of formula I in the control of insects and acarines include:

to growing crops as foliar sprays, dusts, granules and foams; and as suspensions of finely divided and encapsulated compounds of formula I; as soil and root treatments by liquid drenches, dusts, granules, smokes and foams; and as seed dressings by liquid slurries and dusts.

to stored products, timber and household goods as sprays, dusts and smokes, or incorporated into strips of polymers; as poisoned baits for the control of grasshoppers and locusts and other arthropod pests.

to persons or animals infested by or exposed to infestation by arthropods or to their immediate vicinity (e.g. housing) as sprays, baths, jets, dips, showers, fogs, dusts, livestock self-treatment systems, greases, wax-smears, creams and shampoos, or to persons or animals infested by or exposed to infestation by arthropods by parenteral or oral administration (e.g. incorporated in feed or suitable pharmaceutical formulations), or to the environment in general or in specific locations where pests may lurk as sprays, fogs, dusts, greases, wax-smears, smokes, lacquers, granules and trickle feeds to waterways.

The present invention includes within its scope pharmaceutical compositions (including veterinary compositions) which comprise at least one compound of the invention together with a pharmaceutical carrier or coating. In clinical practice the compounds of the present invention will normally be administered orally, rectally, vaginally or parenterally.

Solid compositions for oral administration include compressed tablets, pills, dispersible powders, and granules.

Liquid compositions for oral administration include pharmaceutically acceptable emulsions, solutions, suspensions, syrups and elixirs.

The compositions according to the invention, for oral administration, also include capsules of absorbable material such as gelatin containing one or more of the compounds of the invention.

Solid compositions for vaginal administration include pessaries.

Solid compositions for rectal administration include suppositories.

Preparations according to the invention for parenteral administration include sterile aqueous or non-aqueous solutions, suspensions, or emulsions.

The compounds of the invention may alternatively be administered orally in the form of an aerosol.

Methods of presentation of pharmaceutically active compounds are well known in the art and a suitable vehicle may be determined by the physician, pharmacist or veterinarian, depending upon such factors as the effect sought, the size, age, sex and condition of the patient and, for veterinary uses, species of the animal to be treated, and on the physical properties of the active compound. The compositions may also contain, as is usual in the art, such materials as solid or liquid adjuvants, for example wetting agents, preservatives, flavouring and colouring agents.

The percentage of active ingredient in the compositions of the invention may be varied, it being necessary that if should constitute a proportion such that a suitable dosage for the therapeutic effect desired shall be obtained. Obviously several unit dosage forms may be administered at about the same time.

In general, the compositions for the modification or synchronisation of functions of female mammalian reproductive systems should normally contain at least 0.025% by weight of active substance when required for administration by injection; for oral administration the preparations will normally contain at least 0.1% by weight of active substance.

The dose employed depends upon the desired therapeutic effect, the route of administration and the duration of the treatment. The doses are generally, for example, between 1 $\mu$g and 50 mg/kg body weight by intravaginal or intracervical administration, between 0.1 $\mu$g and 2.0 mg/kg body weight by intravenous administration, and between 10 $\mu$g and 10 mg/kg body weight orally.

If necessary these doses may be repeated as and when required.

The following Example illustrates pharmaceutical compositions according to the invention.

EXAMPLE 8

Witepsol S-58 (a pessary-base supplied by Dynamit Nobel A.G.) (2 g) was melted at below 40° C. and there was added to it (R)-2-hydroxy-2,6-dimethyl-11-phenoxyundec-8-trans-en-10-one (2 mg). After mixing to form a suspension, the suspension was poured into a pessary mould and cooled until the suspension became solid.

According to a further feature of the invention, there are provided compositions suitable for use against insects and acarines containing as active ingredient at least one of the compounds of formula I in association with one or more diluents compatible with the compounds of formula I.

Solid compositions according to the invention suitable for use as aforesaid and for application to growing crops or crop-growing loci contain at least one compound of formula I admixed with one or more solid diluents.

Suitable solid diluents include aluminium silicate, kieselguhr, corn husks, tricalcium phosphate, powdered cork, adsorbent carbon black, magnesium silicate, a clay such as kaolin, bentonite or attapulgite, and water soluble polymers, and such solid compositions may, if desired, contain one or more compatible wetting, dispersing, emulsifying or colouring agents which, when solid, may also serve as diluent.

Such solid compositions may take the form of, for example, dusts, granules or wettable powders.

Liquid compositions for application to growing crops and crop-growing loci according to the invention may take the form of solutions, suspensions and emulsions of one or more of the compounds of formula I, optionally encapsulated in natural or synthetic polymers, and may, if desired, incorporate wetting, dispersing or emulsifying agents.

Compositions in the form of aerosols containing one or more of the compounds of formula I are also within the scope of the present invention.

If desired, the compositions according to the present invention suitable for use against insects and acarines may contain other adjuvants such as adhesives.

The liquid compositions hereinbefore described for application to growing crops and crop-growing loci may, in general, alternatively be employed as trickle feedstocks to treat flowing water. Standing or flowing waters may also be treated with compounds of formula I formulated in homogenous or heterogenous granules, pellets or capsules designed to release their active constituents over a period of time.

The compositions hereinbefore described for application to growing crops and crop-growing loci may, in general, alternatively be employed for topical application to man and animals and in the protection of stored products, household goods, property and areas of the general environment.

Solid compositions in the form of dusts hereinbefore described for application to growing crops or crop-growing loci may, in general, alternatively be employed contained in bags or sacks in such a manner as to permit self-treatment by cattle.

Oily solutions may be applied to backrubbers used by cattle to achieve self-medication by them.

Compositions in the form of solutions or suspensions together, if desired, with additives as described above, in vegetable oil or other greases, paraffin wax or other waxes, or lacquers or creams, for application to large or small animals or parts thereof to control or prevent attacks by arthropods are also included in the invention.

According to a further feature of the invention, there are provided solid or liquid baits suitable for insecticidal and acaricidal use comprising at least one compound of formula I. The bait employed in addition to the carrier or diluent material, which may include a food substance to induce consumption, may include any substance to which the insect or acarine is attracted.

Compositions according to the present invention may also contain herbicides, fungicides, other insecticides and acaricides, fertilisers, antiseptic agents, bacteriostats, bactericidal agents, sporticidal agents and auxiliary therapeutic agents.

The compositions for use against insects and acarines according to the invention usually contain between 0.0001% and 95%, more particularly between 0.0005% and 50%, by weight of at least one of the compounds of formula I. The actual compositions employed and their rate of application shall be those considered necessary to achieve the desired effect(s) by the farmer, livestock producer, medical or veterinary practitioner, pest control operator or other person skilled in the art. Solid and liquid compositions for application to growing crops and crop-growing loci, topically to animals, to timber and to stored products, household goods and their environs usually contain between 0.0005% and 50%, more particularly between 0.01% and 10%, by weight of compounds of formula I.

The following Examples illustrate compositions for the control of insects and acarines according to the present invention.

EXAMPLE 9

Granules of the following constitution were prepared by the application of known methods.

| | |
|---|---|
| (R)-12-(3-chlorophenyl)-2-hydroxy-2,6-dimethyldodec-8-trans-en-10-one | 5% w/w |
| Waxoline Red OS (a red azo dye) | 0.2% w/w |
| 30/60 Attaclay granules (sorptive silica clay) | to 100% by weight. |

EXAMPLE 10

A water soluble concentrate of the following constitution was prepared by the application of known methods.

| | |
|---|---|
| (6R,10RS)-2,6-dimethylpentadec-8-trans-ene-2,10-diol | 10% w/v |
| Ethylan KEO (nonylphenol ethylene oxide condensate) | 10% w/v |
| dimethylformamide | to 100% by volume. |

We claim:

1. A tertiary alcohol of the formula:

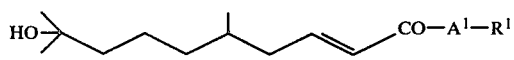

wherein either (i) $A^1$ represents a direct bond and $R^1$ represents a phenyl group or a phenyl group carrying one or two substituents selected from halogen atoms, alkyl and alkoxy groups, each containing from 1 to 4 carbon atoms, and the trifluoromethyl group or (ii) $A^1$ represents an alkylene group containing from 1 to 10 carbon atoms and $R^1$ represents a phenyl, phenoxy, or phenylthio group carrying one or two substituents selected from halogen atoms, alkyl and alkoxy groups, each containing from 1 to 4 carbon atoms, and the trifluoromethyl group.

2. A tertiary alcohol according to claim 1 selected from the group consisting of (R)-11-(4-chlorophenoxy)-2-hydroxy-2,6-dimethylundec-8-trans-en-10-one, (R)-2-hydroxy-2,6-dimethyl-10-phenyldec-8-trans-en-10-one, (R)-10-(4-bromophenyl)-2-hydroxy-2,6-dimethyldec-8-trans-en-10-one, (R)-12-(3-trifluoromethylphenyl)-2-hydroxy-2,6-dimethyldodec-8-trans-en-10-one, (R)-2-hydroxy-2,6-dimethyl-11-phenylundec-8-trans-en-10-one, (R)-12-(2-chlorophenyl)-2-hydroxy-2,6-dimethyldodec-8-trans-en-10-one, (R)-2-hydroxy-2,6-dimethyl-11-phenylthioundec-8-trans-en-10-one, and (R)-2-hydroxy-2,6-dimethyl-13-phenoxytridec-8-trans-en-10-one.

3. A tertiary alcohol according to claim 1 wherein $A^1$ represents a straight-chain alkylene group containing from 1 to 3 carbon atoms.

4. A tertiary alcohol according to claim 1 wherein $R^1$ represents a phenyl or phenoxy group, or a phenyl or phenoxy group substituted by a halogen atom.

5. A tertiary alcohol according to claim 1 wherein $R^1$ represents a phenyl or phenoxy group substituted by a chlorine atom.

6. A tertiary alcohol according to claim 1 which is (R)-2-hydroxy-2,6-dimethyl-11-phenoxyundec-8-trans-en-10-one.

7. A tertiary alcohol according to claim 1 which is (R)-11-(2-chlorophenoxy)-2-hydroxy-2,6-dimethylundec-8-trans-en-10-one.

8. A tertiary alcohol according to claim 1 which is (R)-2-hydroxy-2,6-dimethyl-13-phenyltridec-8-trans-en-10-one.

9. A tertiary alcohol according to claim 1 which is (R)-2-hydroxy-2,6-dimethyl-12-phenyldodec-8-trans-en-10-one.

10. A tertiary alcohol according to claim 1 which is (R)-11-(3-chlorophenoxy)-2-hydroxy-2,6-dimethylundec-8-trans-en-10-one.

11. A tertiary alcohol according to claim 1 wherein $A^1$ represents a straight chain alkylene group of 1 to 3 carbon atoms and $R^1$ represents phenyl or phenoxy which are unsubstituted or substituted by a chlorine atom.

12. A tertiary alcohol according to claim 1 which is (R)-12-(4-chlorophenyl)-2-hydroxy-2,6-dimethyldodec-8-trans-en-10-one.

13. A tertiary alcohol according to claim 1 which is (R)-12-(3-chlorophenyl)-2-hydroxy-2,6-dimethyldodec-8-trans-en-10-one.

14. A composition suitable for use against insects and acarines which comprises, as active ingredient, a tertiary alcohol as claimed in claim 1 in association with one or more diluents compatible with the said compound.

15. The use of a tertiary alcohol as claimed in claim 1 for the control of insects and acarines.

* * * * *